United States Patent
Ho et al.

(10) Patent No.: US 7,026,350 B2
(45) Date of Patent: Apr. 11, 2006

(54) WATER-SOLUBLE DRUGS AND METHODS FOR THEIR PRODUCTION

(75) Inventors: David K. Ho, North Potomac, MD (US); Raya Mandler, Bethesda, MD (US); Ada Belinda Alvarado-Lindner, Frederick, MD (US); Kaye B. Dillah Upadhyay, Gaithersburg, MD (US); David J. Newman, Wayne, PA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/837,785

(22) Filed: May 3, 2004

(65) Prior Publication Data

US 2004/0204395 A1 Oct. 14, 2004

Related U.S. Application Data

(62) Division of application No. 09/743,873, filed as application No. PCT/US99/16199 on Jul. 15, 1999, now Pat. No. 6,747,055.

(60) Provisional application No. 60/093,284, filed on Jul. 17, 1998.

(51) Int. Cl.
*C07D 225/04* (2006.01)
*A61K 47/48* (2006.01)
*A61P 35/00* (2006.01)

(52) U.S. Cl. ..................... 514/425; 540/461
(58) Field of Classification Search .............. 540/461; 514/425
See application file for complete search history.

(56) References Cited

U.S. PATENT DOCUMENTS

| | | | |
|---|---|---|---|
| 4,261,989 A | 4/1981 | Sasaki et al. | |
| 5,087,616 A | 2/1992 | Myers et al. | |
| 5,387,584 A | 2/1995 | Schnur | |
| 5,606,030 A | 2/1997 | Emini et al. | |
| 5,610,140 A | 3/1997 | Goodfellow et al. | |
| 5,646,131 A | 7/1997 | Badwan et al. | |

FOREIGN PATENT DOCUMENTS

| | | |
|---|---|---|
| WO | WO 94/06750 | 3/1994 |
| WO | WO 96/40251 | 12/1996 |

OTHER PUBLICATIONS

Schnur et al. (Journal of Medicinal Chemistry (1995), 38, 3806-3812).*
Hawthorne et al., "Liposomes as Drug Delivery Vehicles for Boron Agents," *J. Neurooncol.*, 33(1-2), 53-58 (May 1997).
Schacter et al., "Clinical and Pharmacokinetic Overview of Parenteral Etoposide Phosphate," *Cancer Chemother. Pharmacol.*, 34 Suppl., S58-63 (1994).
Sweetana et al., "Solubility Principles and Practices for Parenteral Drug Dosage Form Development," *PDA J. Pharm. Sci. & Tech.*, 50, 330 (1995).

* cited by examiner

*Primary Examiner*—Bruck Kifle
(74) *Attorney, Agent, or Firm*—Leydig, Voit & Mayer. Ltd.

(57) ABSTRACT

The present invention relates to water-soluble drugs, compositions containing same, and, in particular, a water-soluble analogue of geldanamycin. This invention also relates to a method of producing water-soluble analogues of water-insoluble drugs through derivatization and conjugation with a polar moiety via a thiol ether bond with a heterobifunctional linking molecule.

40 Claims, 1 Drawing Sheet

WATER-SOLUBLE DRUGS AND METHODS FOR THEIR PRODUCTION

RELATED APPLICATIONS

This application is a divisional of U.S. patent application No. 09/743,873, now U.S. Pat. No. 6,747,055, filed Apr. 18, 2001, which is the national stage filing of PCT/US99/16199, filed Jul. 15, 1999, which claims the benefit of U.S. Provisional Patent Application No. 60/093,284, filed Jul. 17, 1998.

TECHNICAL FIELD OF THE INVENTION

The present invention relates to water-soluble drugs, in particular water-soluble analogues of geldanamycin, and compositions comprising the same. This invention also relates to a method of rendering water-insoluble drugs soluble in water and a method of treating cancer.

BACKGROUND OF THE INVENTION

A common problem associated with drugs intended for parenteral, and especially intravenous, administration has been the solubilization of a slightly soluble or water-insoluble active ingredient (Sweetana et al., PDA *J. Pharm. Sci. & Tech.*, 50, 330 (1995)). As a result, many drugs of potential benefit in cancer chemotherapy and other areas of therapeutics have been abandoned. Methods have been developed whereby drugs can be enveloped in micelles and placed into aqueous solutions (Hawthorne et al., *J. Neurooncol.*, 33, 53–58 (1997)). Likewise, cosolvents and complexing agents allow some drugs to be dissolved in water (Badwan et al., U.S. Pat. No. 5,646,131). The use of these reagents, however, can be complex and have negative attributes due to the additional reagent required to dissolve the active ingredient (Sweetana et al. (1995), supra). Prodrugs also have been developed by attaching groups, such as phosphates and other conjugates, to increase their solubility and enhance their performance (Schacter et al., *Cancer Chemother. Pharmacol.*, 34, S58 (1994); Kingston et al., U.S. Pat. No. 5,278,324).

One water-insoluble drug of potential beneficial use in cancer therapy is geldanamycin. The drug is an ansamycin isolated from the broth of *Streptomyces hygroscopicus* var. *geldanus* (DeBoer et al., *Antiobiot.*, 23, 442 (1970)). It has been found to exert its antiproliferating and anticancer activities by binding with the heat shock protein 90 (Hsp90) chaperone and, in turn, altering the translocation properties of the tumor suppressor protein p53 (Stebbins et al., *Cell*, 239 (1997); Sepehrnia et al., *J. Biol. Chem.*, 271, 15,084 (1996); Dasgupta et al., *Experimental Cell Research*, 29, 237 (1997)). Despite its therapeutic potential as an anticancer agent, initial studies indicate that the bioavailability of geldanamycin must be enhanced and the toxicity associated with the natural product reduced before significant progress can be made with respect to the anticancer use of geldanamycin. Chemical modifications of geldanamcyin could potentially provide analogs with improved bioactivity and bioavailability. While derivatives of geldanamycin have been developed to enhance the cancer-fighting effects of the drug, the low solubility of such derivatives have required the use of emulsifying or suspending agents in order to obtain aqueous solutions. This has tended to reduce the bioavailability of the drug, and has thereby affected its utility as an anticancer agent.

The present invention addresses these problems by providing a method of producing water-soluble analogues of water-insoluble drugs and, in particular, by providing a water-soluble analogue of the anticancer drug geldanamycin. Due to its thiol ether linkage, the analogue is expected to exhibit superior bioavailability and stability under physiological conditions.

BRIEF SUMMARY OF THE INVENTION

The present invention provides a water-soluble compound of the formula

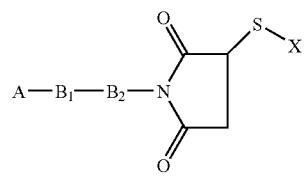

where A is a water-insoluble drug, $B_1$ and $B_2$ together are a spacer moiety, and X is a polar moiety. The invention further provides a pharmaceutical composition comprising a pharmaceutically acceptable carrier and the above-described compound. In addition, the present invention provides a method of treating cancer in a mammal. The method comprises administering to a mammal having cancer an effective amount of the above-described compound.

The present invention further provides a method of rendering soluble in water a water-insoluble drug. The method comprises contacting a water-insoluble drug comprising a side-chain that can react with a bifunctional linking molecule with a bifunctional linking molecule comprising a maleimido functional group to obtain a first derivative of the water-insoluble drug comprising a side-chain that comprises a maleimido functional group. The method further comprises contacting the first derivative with a polar moiety comprising a thio group (X—SH) to obtain a water-soluble compound as described above.

The present invention still further provides a water-soluble compound of the formula

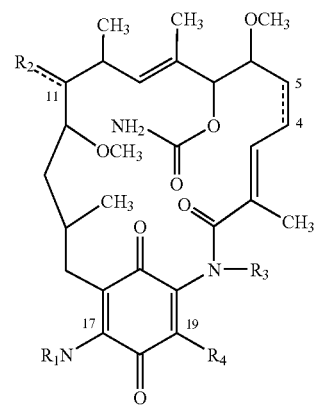

or a pharmaceutically acceptable salt thereof, wherein:

$R_1$ is an ionic moiety bound to the carbon at position 17 via a nitrogen atom, $R_2$ is a halo or an —$OR_8$ when there is a single bond between $R_2$ and the carbon at position 11, wherein $R_8$ is hydrogen, a $C_1$–$C_8$ alkylamido, a $C_1$–$C_8$ alkyl, a $C_2$–$C_8$ alkenyl, a $C_2$–$C_8$ alkynyl, a $C_1$–$C_8$ hydroxyalkyl, a $C_1$–$C_8$ alkyl carbamoyl, a $C_1$–$C_8$ alkylcarbonyl, or an aralkyl, any of which $R_8$ can be further substituted with one or more substituents, which can be the same or different, selected from the group consisting of a nitro, a halo, an azido, a hydroxy, an amido and an amino group, or $R_2$ is oxo (=O) or oximino (=NOH) when there is a double bond between $R_2$ and the carbon at position 11, $R_3$ is selected from the group consisting of hydrogen and a group of the formula

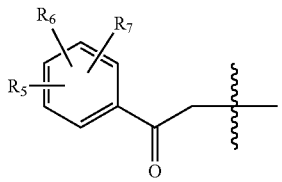

wherein $R_5$, $R_6$, and $R_7$ are each independently selected from the group consisting of hydrogen, a halo, an azido, a nitro, a $C_1$–$C_8$ alkyl, a $C_1$–$C_8$ alkoxy, an aryl, a cyano, and an $NR_{10}R_{11}R_{12}$, wherein $R_{10}$, $R_{11}$, and $R_{12}$ are each independently selected from the group consisting of hydrogen and a $C_1$–$C_3$ alkyl, $R_4$ is selected from the group consisting of hydrogen, a halo, a $C_1$–$C_8$ alkylamino, and a $C_1$–$C_8$ dialkylamino, and the bond between the carbons at positions 4 and 5 can be a single bond or a double bond.

Also provided by the present invention is a water-soluble compound of the formula

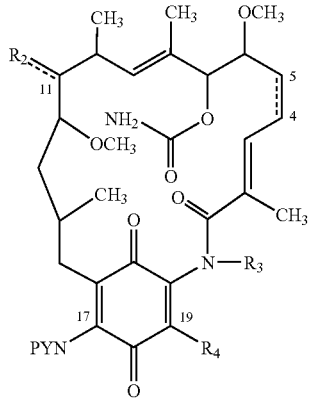

or a pharmaceutically acceptable salt thereof, wherein:

Y is a spacer group,

P is a polypeptide or a protein that selectively binds to the surface of a mammalian cell, $R_2$ is a halo or an —$OR_8$ when there is a single bond between $R_2$ and the carbon at position 11, wherein $R_8$ is selected from the group consisting of hydrogen, a $C_1$–$C_8$ alkylamido, a $C_1$–$C_8$ alkyl, a $C_2$–$C_8$ alkenyl, a $C_2$–$C_8$ alkynyl, a $C_1$–$C_8$ hydroxyalkyl, a $C_1$–$C_8$ alkyl carbamoyl, a $C_1$–$C_8$ alkylcarbonyl, and an aralkyl, any of which $R_8$ groups can be further substituted with one or more substituents, which can be the same or different, selected from the group consisting of a nitro, a halo, an azido, a hydroxy, an amido and an amino group, or $R_2$ is oxo (=O) or oximino (=NOH) when there is a double bond between $R_2$ and the carbon at position 11, $R_3$ is selected from the group consisting of hydrogen and a group of the formula

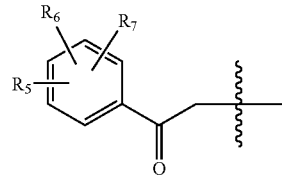

wherein $R_5$, $R_6$, and $R_7$ are each independently selected from the group consisting of hydrogen, a halo, an azido, a nitro, a $C_1$–$C_8$ alkyl, a $C_1$–$C_8$ alkoxy, an aryl, a cyano, and an $NR_{10}R_{11}R_{12}$, wherein $R_{10}$, $R_{11}$, and $R_{12}$ are each independently selected from the group consisting of hydrogen and a $C_1$–$C_3$ alkyl, $R_4$ is selected from the group consisting of hydrogen, a halo, a $C_1$–$C_8$ alkylamino, and a $C_1$–$C_8$ dialkylamino, and the bond between the carbons at positions 4 and 5 can be a single bond or a double bond.

DETAILED DESCRIPTION OF THE INVENTION

Figure 1:
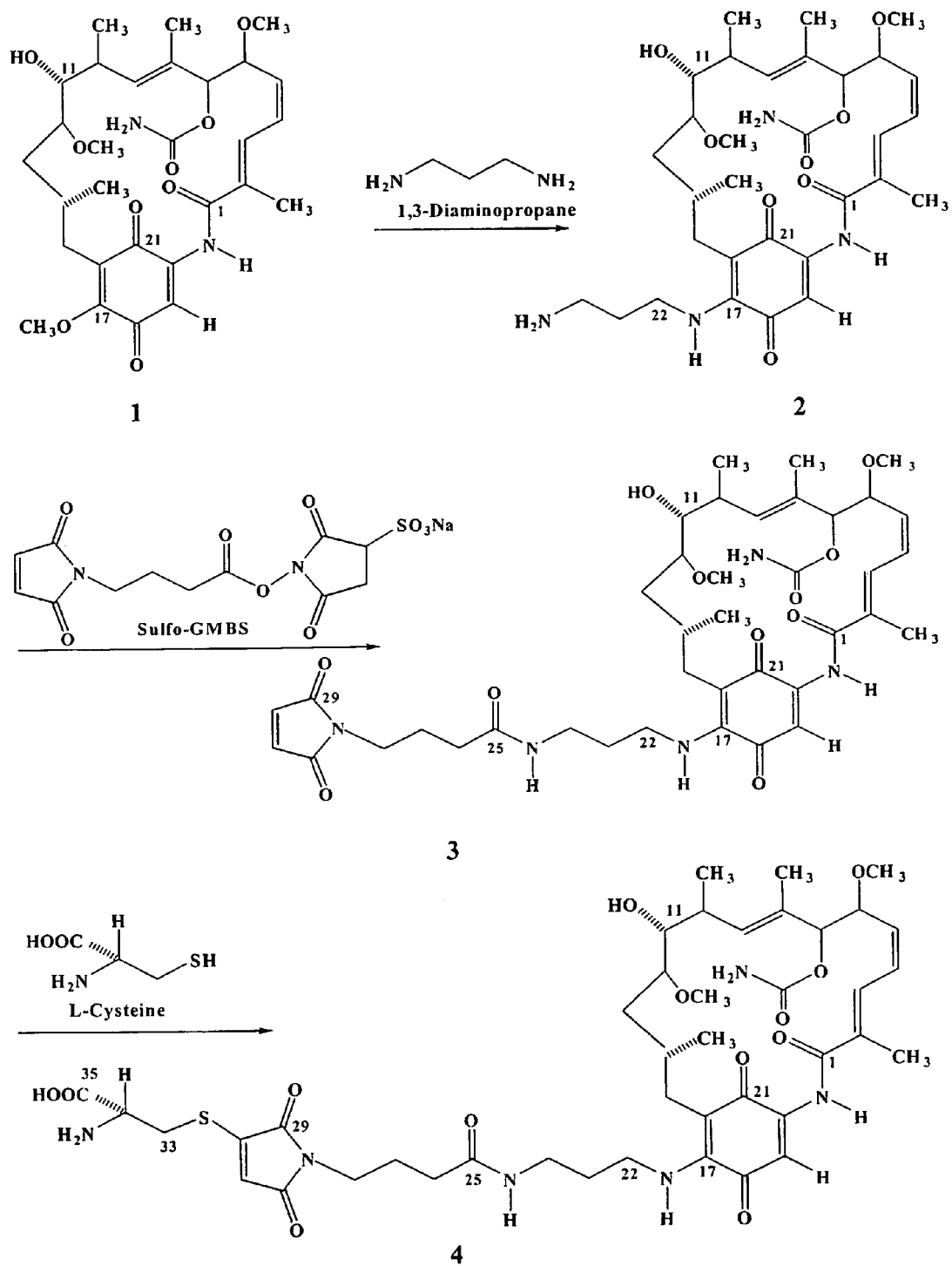
FIG. 1 is a reaction scheme illustrative of the present inventive method by which the water-insoluble geldanamycin derivative is rendered water-soluble.

The present invention provides water-soluble compounds, in particular, a water-soluble analogue of geldanamycin, compositions comprising such water-soluble compounds and a method of producing water-soluble analogues of water-insoluble drugs. Also provided is a method of using such compounds to treat cancer.

Water-Soluble Drugs

The present inventive water-soluble compound has the formula

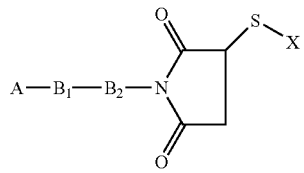

or a pharmaceutically acceptable salt thereof, wherein A is a water-insoluble drug, $B_1$ and $B_2$, together, are a spacer moiety, and X is a polar moiety. $B_2$ can be any suitable group lending a distance of at least one carbon atom, and preferably less than twenty carbon atoms (e.g., one to ten carbon atoms), between the water-insoluble drug and the maleimido functional group. Preferably, $B_2$ is selected from the group consisting of a $C_1$–$C_{19}$ alkylamido, a $C_1$–$C_{19}$ alkyl, a $C_2$–$C_{19}$ alkenyl, a $C_2$–$C_{19}$ alkynyl, a $C_1$–$C_{19}$ hydroxyalkyl, a $C_1$–$C_{19}$ alkycarbamoyl, a $C_1$–$C_{19}$ alkylcarbonyl, and an aralkyl, any of which can be further substituted with one or more substituents, which can be the same or different, selected from the group consisting of a nitro, a halo, an azido, a hydroxy, an amido and an amino group. As meant herein and throughout this disclosure an "aralkyl" moiety is preferably a $C_1$–$C_{20}$ alkyl, and more preferably a $C_1$–$C_8$ alkyl, wherein an alkyl hydrogen atom is replaced by an aryl as defined herein. Examples of aralkyl radicals include benzyl, phenethyl, 1-phenylpropyl, 2-phenylpropyl, 3-phenylpropyl, 1-naphthylpropyl, 2-naphthylpropyl, 3-naphthylpropyl, 3-naphthylbutyl, and the like. The term "aryl" refers to an aromatic carbocyclic radical, as commonly understood in the art, and includes monocyclic and polycyclic aromatics such as, for example, phenyl and naphthyl radicals, which radicals are, unless indicated otherwise, optionally substituted with one or more substituents, which are the same or different, selected from the group consisting of a halogen, an alkyl, an alkoxy, an amino, a cyano, a nitro, and the like. Preferably, the aryl moiety has one or more six-membered carbocyclic rings including, for example, one to three carbocyclic rings, such as phenyl, naphthyl, and biphenyl.

More preferably $B_2$ is selected from a group consisting of a $C_1$–$C_7$ alkylamido, a $C_1$–$C_7$ alkyl, a $C_2$–$C_7$ alkenyl, a $C_2$–$C_7$ alkynyl, a $C_1$–$C_7$ hydroxyalkyl, a $C_1$–$C_7$ alkylcarbamoyl, a $C_1$–$C_7$ alkylcarbonyl, or an aralkyl, wherein the aralkyl has one to three aryl ring structures having 5 or 6 ring atoms each, and the alkyl portion of the aralkyl moiety has one to eight carbon atoms, and any wherein any of the foregoing $B_2$ groups can be further substituted with one or more substituents, which can be the same or different, selected from the group consisting of a nitro, a halo, an azido, a hydroxy, an amido or an amino group.

$B_1$ can be a methylenyl, an amido, —N═, an amino, or a thiol maleimido group. $B_1$ is ordinarily derived from a suitable functional group incorporated into a bifunctional (i.e., dimaleimido or heterobifunctional) linking molecule. Of course, the bifunctional linking molecule can be one that is commercially available, such as those available from Pierce, Rockford, Ill. Commercially available bifunctional linking moieties tend to contribute a portion of the functional group to the molecules that form from their use in linking reactions. Exemplary linking reactions giving rise to some of these embodiments are depicted in the EXAMPLES section (below). A multiplicity of spacer groups can thereby be incorporated into the present inventive water-soluble drug. One particular spacer group useful in the context of the present invention has the following structure:

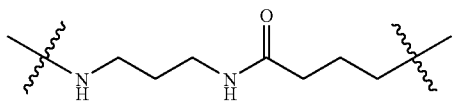

X can be any group that exhibits polar characteristics, including, but not limited to, the propensity to interact with other polar substances through hydrogen-bonding forces, Van der Waals forces, or dipole moments. X together with the remainder of the present inventive compound, is such that the present inventive compound is water-soluble. For purposes of the present invention, X is preferably ionic, more preferably zwitterionic at neutral pH. Preferably, ionic polar moieties are charged (e.g., greater than about 50% charged) at neutral pH. For zwitterionic polar moieties, it is preferable for the charges to be balanced at a pH of about 4 to about 10. More preferably, the zwitterionic moiety has a zero net charge (i.e., balanced charges) at a pH of about 6 to about 8. Additionally, the zwitterionic moiety preferably has at least about 0.8 negative charges and at least about 0.8 positive charges. By way of example and for the purposes of this invention, NaCl in water contains 1.0 positive charge and 1.0 negative charge.

Polypeptides, peptides, and amino acids tend to be polar, and frequently zwitterionic moieties and are useful in the context of the present invention. Proteins suitable for use in the context of the present invention comprise polypeptides incorporating amino acids that exist in a conformation associated with a biological function or structure that is characteristic of a substantially similar molecule produced by a living cell. Preferred amino acids useful in the context of the present invention include lysine and cysteine, in particular L-cysteine, because they contain reactive side-chain nitrogen and sulfur atoms, respectively, that react easily with the functional portions of commercially available linker molecules.

Any water-insoluble drug can be used in the context of the present invention. For the purposes of this invention, the term "drug" means any compound which is biologically active, e.g., exhibits a therapeutic or prophylactic effect in vivo, or a biological effect in vitro. For example, the drug can be an antihypertension drug, an antibiotic drug, or an anticancer drug. The present invention is particularly useful for rendering macrolide and ansamacrolide drugs water-soluble, at least in part because the efficacy of these drugs tends to be limited by the amount of the drug that can be administered without causing an anaphylactic-like response (sometimes called a "toxic manifestation" by those skilled in the art in the context of cancer chemotherapy or the administration of insoluble drugs). An anaphylactic-like response occurs when a water-insoluble drug, or a drug that readily precipitates at pharmacoactive concentrations in a mammal's blood is administered at above a minimum threshold rate or concentration. As is known in the art, an anaphylactic-like response is accompanied by severe toxicity, swelling at the site of administration, nausea and other serious side-effects in a mammal. Geldanamycin, and geldanamycin derivatives, are particularly useful in conjunction with the present invention. Examples of geldanamycin derivatives that are useful in the context of the present invention are described elsewhere herein, and in U.S. Pat. No. 5,387,584 (to Schnur) and U.S. Pat. No. 4,261,989 (to Sasaki et al.), which also disclose methods for making geldanamycin derivatives.

The term "water-insoluble" as used herein means partially or completely insoluble in water, or partially or completely non-dispersible in water. A water-insoluble compound in the context of the present invention preferably has a solubility less than the minimum effective concentration in physiological saline. In contrast, a "water-soluble" compound of the present invention preferably has a solubility equal to, or greater than, the minimum clinically-effective concentration in physiological saline. A clinically-effective concentration of a derivative of an insoluble drug is a concentration that is less than the concentration that will induce an anaphylaxis-like response in a patient, and equal to, or greater than, the minimum concentration at which a therapeutic effect can be observed. Preferably, the inventive water-soluble compound is soluble to at least about 2 mM in physiological saline, more preferably to at least about 6 mM in physiological saline. A water-insoluble drug useful in the context of the present invention preferably has a solubility of less than about 2 mM, and optionally has a solubility of less than about 0.02 mM, in physiological saline. Of course, the skilled artisan will appreciate that for any particular drug of interest, these concentrations can be empirically determined and can be higher or lower. Preferably, the present inventive water-soluble drug is at least 3% as active as the water-insoluble drug from which it is obtained, and more preferably is at least 10% as active as the water-insoluble drug.

The present inventive compound can be in the form of a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example p-toluenesulphonic acids.

Ionic Geldanamycin

The present invention also provides water-soluble derivatives of geldanamycin of the formula:

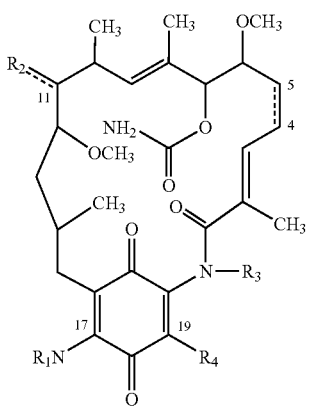

wherein $R_1$, $R_2$, $R_3$, and $R_4$ are defined below.

$R_1$ is an ionic moiety bound to the carbon at position 17 via a nitrogen atom. Preferably, the ionic moiety promotes solubility in water. Additionally, $R_1$ is preferably an aliphatic moiety that can, but need not, comprise an aryl moiety and is substituted by one or more charged moieties. Preferred aliphatic moieties in the context of the present invention comprise organic molecules comprising less than about 200 carbon atoms and biopolymers, as that term is commonly understood in the art, including, but not limited to, proteins, nucleic acids, and polysaccharides. The charged moieties can be the same or different and can be selected from the group consisting of carbamate, carbonate, carboxylate, phosphamate, phosphate, phosphonate, pyrophosphate, triphosphate, sulfamate, sulfate, sulfonate, a $C_1$–$C_8$ monoalkylamine that is protonated at neutral pH, a $C_1$–$C_4$ dialkylamine that is protonated at neutral pH, and a $C_1$–$C_4$ trialkylammonium. The selection of $R_1$ is preferably made such that it is charged at neutral pH (i.e., about pH 7). Preferably, $R_1$ is selected from the group consisting of a $C_1$–$C_{19}$ alkylamido, a $C_1$–$C_{19}$ alkyl, a $C_2$–$C_{19}$ alkenyl, a $C_2$–$C_{19}$ alkynyl, a $C_1$–$C_{19}$ hydroxyalkyl, a $C_1$–$C_{19}$ alkyl carbamoyl, a $C_1$–$C_{19}$ alkylcarbonyl, and an aralkyl. More preferably, $R_1$ is selected from the group consisting of a $C_1$–$C_7$ alkylamido, a $C_1$–$C_7$ alkyl, a $C_2$–$C_7$ alkenyl, a $C_2$–$C_7$ alkynyl, a $C_1$–$C_7$ hydroxyalkyl, a $C_1$–$C_7$ alkyl carbamoyl, a $C_1$–$C_7$ alkylcarbonyl, and a monocarbocyclic aralkyl. Additionally, $R_1$ can comprise a nucleoside (including nucleotides), a saccharide (including disaccharides, trisaccharides, and, as suggested above, polysaccharides of 4 to about 50 or 200 sugar residues). $R_1$ also can comprise an amino acid, in particular a naturally occurring amino acid, such as one encoded by a mammalian genome, in particular a human genome. Of these, lysine is among the preferred amino acids because the epsilon-amino group can displace the 17-methoxy group of geldanamycin to yield a soluble derivative of geldanamycin. Where $R_1$ is an amino acid, suitable blocking groups can be used to protect functional groups on the amino acid. For example, BOC can be used to protect the α-amino group of the amino acid (see, King et al., *Bioconjugate Chem.*, 10, 279–88 (1999)). The "blocked" 17-demethoxy-17-BOC-amino acid-geldanamycin can optionally be "unblocked" in accordance with methods well-known in the art. Additionally, it is preferable that $R_1$ be zwitterionic at neutral pH. Any of these $R_1$ moieties can be further substituted with one or more substituents, which can be the same or different, selected from the group consisting of a nitro, a halo, an azido, a hydroxy, an amido and an amino group.

$R_2$ can be a halo or —$OR_8$, in which case there is a single bond between $R_2$ and the carbon at position 11. $R_8$ is selected from the group consisting of hydrogen, a $C_1$–$C_8$ alkylamido, a $C_1$–$C_8$ alkyl, a $C_2$–$C_8$ alkenyl, a $C_2$–$C_8$ alkynyl, a $C_1$–$C_8$ hydroxyalkyl, a $C_1$–$C_8$ alkyl carbamoyl, a $C_1$–$C_8$ alkylcarbonyl, and an aralkyl, wherein the alkyl portion of the aryl moiety preferably has one to eight carbon atoms. These $R_8$ groups can be further substituted with nitro, halo, azido, hydroxy, amido or amino groups.

Alternatively, $R_2$ is oxo (=O) or oximino (=NOH), in which case $R_2$ is bonded to the carbon at position 11 via a double bond.

$R_3$ is selected from the group consisting of hydrogen and a group of the formula

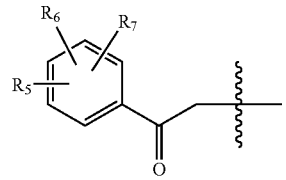

wherein $R_5$, $R_6$, and $R_7$ are each independently selected from the group consisting of hydrogen, a halo, an azido, a nitro, a $C_1$–$C_8$ alkyl, a $C_1$–$C_8$ alkoxy, an aryl, a cyano, and an $NR_{10}R_{11}R_{12}$, wherein $R_{10}$, $R_{11}$, and $R_{12}$ are each independently selected from the group consisting of hydrogen and $C_1$–$C_3$ alkyl.

$R_4$ is selected from the group consisting of hydrogen, a halo, a $C_1$–$C_8$ alkylamino, and a $C_1$–$C_8$ dialkylamino, and the bond between the carbons at positions 4 and 5 can be a single bond or a double bond or can be dihydrogenated.

In one particular embodiment of the present invention, the bond between the carbons at positions 4 and 5 is a double bond, and $R_2$, $R_3$, and $R_4$ are selected to correspond to the homologous groups in geldanamycin such that 17-$R_1$N-17-demethoxy-geldanamycin is obtained. Those skilled in the art will also appreciate that the present invention also comprises 18, 21-dihydroquinones of the present invention. Moreover, embodiments wherein the water-soluble geldanamycin is at least 3% as effective, more preferably at least 10% as effective, as geldanamycin at stopping the proliferation of N87 cells (a gastric carcinoma, from ATCC, Rockville, Md.) in vitro (when measured by the $IC_{50}$ for thymidine incorporation) are preferred. While not intending to be bound by any particular theory, it is believed that 17-demethoxy-17-amino$R_1$ derivatives of geldanamycin are preferable to other derivatives of geldanamycin because they are either pharmaco-active or readily converted to an active form in the cell.

Selectively Targeted Geldanamycin

The present invention also provides a water-soluble compound of the formula:

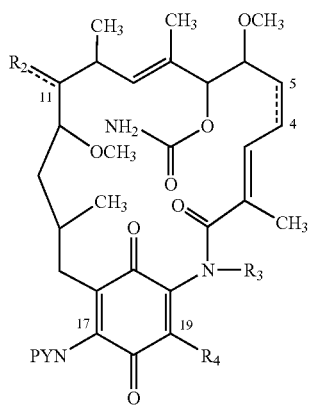

or a pharmaceutically acceptable salt thereof, wherein $R_2$, $R_3$, and $R_4$ are as defined above, Y is a spacer group, and P is a polypeptide or a protein that selectively binds to the surface of a mammalian cell.

Preferably, Y comprises a thio ether. While not intending to be bound by any particular theory, it is believed that thio ether linkages are stable in the blood of a mammal, whereas they are degraded by intracellular enzymes present in cells. One particular Y group useful in the context of the present invention comprises

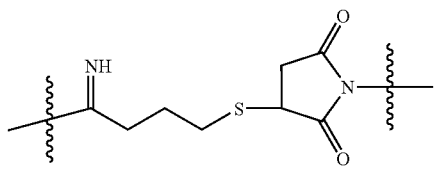

Preferably, this Y moiety comprising the maleimido thiol ether is bonded to P via a lysinyl residue of P. One suitable method for achieving an embodiment of the present invention comprising this Y moiety is depicted in FIG. 1, described below, and a specific embodiment is given in Example 1. This inventive method comprises exposing the protein to a suitable amount of Traut's reagent i.e.,

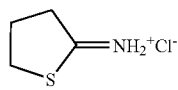

For each protein the amount of Traut's reagent is preferably determined empirically, but can be based on the deductive calculations based on antibody reactions. When P is an antibody (i.e., a protein of about 150 kDa), the molar ratio of Traut's reagent: Ab is at least about 1:1, preferably at least about 5:1, and is preferably less than about 30:1, more preferably less than 15:1. The thiolated protein is highly reactive and should be reacted with a linking molecule as soon as possible. The linking molecule, in turn, is preferably bound to the insoluble drug before the P moiety is thiolated. The reaction of the thiolated protein or polypeptide and the linking molecule is initiated, preferably less than 12 hours after completion of the traut reaction, more preferably less than about 2 hours after the traut reaction. Optionally, the reaction and product can be maintained under inert gas, such as argon.

The reaction of the insoluble drug-linking molecule with the Traut's-derivatized protein is subject to statistical mechanics. Accordingly, any initial preparation (i.e., unpurified preparation) will have a distribution of drug:protein ratios, wherein each molecular product will have a ratio of n:1, wherein n is an integer (unless the protein exists in a complex), and wherein the population has an average ratio of n:m, wherein n and m can be any positive number and need not be integers. However, it will be appreciated that too high or too low a ratio will decrease drug-efficacy and can render the drug or protein completely inactive. Accordingly, the ratio of drug:protein is preferably carefully controlled.

Preferably, the drug to protein ratio, especially when P is an antibody, is at least 0.1:1 (drug:protein), more preferably at least 0.5:1, and more preferably at least 1:1. Additionally, the drug:protein ratio should preferably be less than about 6:1, and more preferably less than about 3:1. Moreover, for smaller proteins and polypeptides of about 10 kDa or less, these ratios are preferably decreased, such that the most preferred ratio is about 0.6 to about 1.4 (drug:protein).

In accordance with this inventive method, a preferred linking moiety comprising a 2-maleimido thiol ether with the structural formula

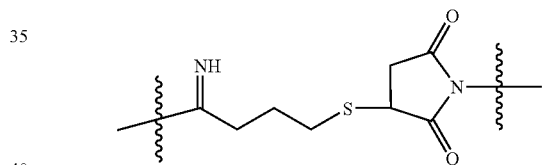

can be made.

Optionally, P can be a polypeptide or a protein that binds to an antigen. One suitable example of such a polypeptide or protein which is useful in the context of the present invention is an antibody, or an antigenically reactive fragment thereof, which is optionally humanized. Examples of suitable antibodies include herceptin and e21. Herceptin is a monoclonal antibody that has been humanized according to methods known in the art and which binds to, and is internalized by, cells expressing the Her2 receptor. The antibody e21 (C. R. King, Georgetown University, Washington, D.C., U.S.A.) is also an antibody that binds to Her2 and is internalized by cells expressing the Her2 receptor. The e21 antibody was raised in mice challenged with a membrane preparation of Her2-transfected mammalian cells in tissue culture. Equivalent antibodies can be raised according to standard methods known in the art.

Embodiments wherein P is an anti-Her2 antibody, or an antigenically reactive fragment thereof, are useful in the treatment of cancer, particularly breast cancer, ovarian cancer, lung cancer, and gastric cancer. Anti-Her2 antibodies per se, exhibit anti-proliferative effects on Her2-expressing cancer cells. In this regard, herceptin is currently approved for clinical use in the therapeutic treatment of cancer and is expected to be of particular utility in the treatment of metastatic breast cancer. Surprisingly, when geldanamycin is linked through a linking moiety, preferably one containing a thiol ether linkage, the anti-proliferative effects against breast cancer cells, e.g., SKBr3 cells (ATCC, Rockville, Md.), MDA-361/DYT2 (a subclone of the well-known MDA-MB-361 cells which were selected for their ability to form tumors in athymic mice by repeated in vivo transfer), and N87 cells, is more effective at inhibiting the growth of the cancer cells than either of the antibody or geldanamycin (used at comparable concentrations) alone. Moreover, the toxicity of the selectively targeted geldanamycin is substantially reduced in mammals because the conjugated geldanamycin is soluble and does not tend to induce an anaphylaxis-like response. Additionally, the adult T-cell leukemia (ATL) cell, HuT102, which is a Her2-negative cancer cell that is highly sensitive to unconjugated geldanamycin, is not sensitive to the selectively targeted geldanamycin compound of the present invention. Thus, the therapeutic index of geldanamycin and of anti-proliferative antibodies can be substantially increased by conjugation of these moieties in accordance with the present invention. While not intending to be bound by any particular theory, it is believed that the ability of e21, herceptin, and other antibodies to be efficiently internalized by target cells substantially enhances the therapeutic effect of the present inventive selectively targeted geldanamycin. Preferably, the selectively targeted geldanamycin is internalized by a mammalian cell that has a receptor for P at least five times more efficiently than another mammalian cell, or an otherwise identical cell, that does not have a receptor for P. Preferably, the selectively targeted geldanamycin of the present invention is internalized by a log phase-target cell in culture at least about 25% as rapidly as an e21:gekdanamycin conjugate of the present invention is internalized into a log phase N87 cell grown in complete RPMI comprising 10% fetal calf serum, glutamine and antibiotics.

Other P moieties useful in the context of the present invention are antibodies huB4, C225 (available from Imclone or John Mendlesohn, Memorial Sloan-Kettering, New York, N.Y.), BR96, and Zenapax. The antibody huB4 (see, Chari et al., *Cancer Research,* 55, 4079–84 (1995); Stone et al., *Blood,* 88, 1188–97 (1996)) is a humanized anti-B4 antibody that binds with high affinity to CD19 and is internalized by cells to which it binds through CD19. The antibody C225 binds with high affinity to human epidermal growth factor receptor and is internalized by cells to which it binds. C225 sensitizes bound cells to anticancer drugs, but the selectively targeted geldanamycin of the present invention will inhibit the growth of cancer cells more effectively than cancer cells treated with C225 and exposed to a pharmaceutically acceptable concentration of water-insoluble geldanamycin. Br96 is a chimeric human/mouse antibody that binds with high affinity to Lewis-Y antigen and is internalized by cells to which it is bound. Lewis-Y antigen is selectively overexpressed on human carcinoma cells (see, Tolcher, *J. Clinical Oncology,* 17, 478–484 (1999)). Any of these, or similar, antibodies can be P in the present inventive selectively targeted geldanamycin.

In other embodiments of the present inventive selectively targeted geldanamycin P can be a diabody, an Fab, an Fab'$_2$, a single-chain antibody, or a single-chain Fab. These antigen-binding proteins and polypeptides can be made in accordance with methods well-known in the art. Moreover, any antigen-binding protein or polypeptide that is useful in the context of the present invention optionally can be humanized, e.g., the complementarity determining regions of the antigen-binding protein or polypeptide can be preserved, while the remainder of the protein can be replaced by suitable human sequences, in accordance with methods known in the art. Additionally, the antigen-binding protein or polypeptide can be cationized (see, Pardridge et al., *J. Pharmacol. and Exp. Therapeutics,* 286, 548–54 (1998)) by converting carboxyl groups to extended primary amino groups. Additionally, Fv's and other antigen-binding proteins or polypeptides of the present invention can be stabilized by treatment with disulfide (see, Reiter et al, *J. Biol. Chem.,* 269, 18327 (1994)). Other suitable modifications of the antigen-binding protein are also known in the art.

Additionally, the moiety P of the present inventive selectively targeted geldanamycin can be a non-antigen-binding protein that binds to a mammalian cell and is preferably internalized by that cell. Preferably, the cell has a receptor specific for P that is overexpressed on pathogenic cells. Also preferably, the cell has a receptor for P which is expressed only or mainly on pathogenic cells. For example, P can be a secreted protein or polypeptide, such as an interleukin. Interleukin-2 is a one such suitable interleukin. Alternatively, P can be a growth factor, such as insulin, insulin-like growth factor, tumor necrosis factor, or epidermal growth factor. Other suitable embodiments of P include heregulin (see, Yang et al., *Clinical Cancer Research,* 4, 993–1004 (1998)) and vascular endothelial cell growth factor, its isoforms, and processed forms (see, Olson et al., *Int. J. Cancer,* 73, 865–70 (1997)).

Compositions

Any of the drug-containing compounds of the present invention can be incorporated into a pharmaceutical composition or used in a method of treating cancer as described herein with respect to the present inventive water-soluble drug.

Advantageously, these embodiments of the present invention increase efficacy by increasing geldanamycin concentration in targeted cells and by decreasing the toxicity of the geldanamycin by increasing its solubility. While not desiring to be bound by any particular theory, it is also believed that the toxicity of geldanamycin is reduced in selectively targeted embodiments of the present invention by selectively targeting geldanamycin to selected cells and by sterically blocking the geldanamycin from acting on non-targeted cells by incorporating a bulky substituent at the 17-position of geldanamycin.

The present inventive composition, which is preferably a pharmaceutical composition, comprises a carrier, preferably a pharmaceutically acceptable carrier, and a compound of the present invention. The pharmaceutical composition can comprise more than one active ingredient, such as more than one compound of the present invention, or a compound of the present invention in combination with another pharmaceutically active agent or drug.

The carrier can be any suitable carrier. With respect to pharmaceutical compositions, the carrier can be any of those conventionally used and is limited only by chemico-physical considerations, such as solubility and lack of reactivity with the active compound(s), and by the route of administration. It will be appreciated by one of skill in the art that, in addition to the following described pharmaceutical composition, the compounds of the present inventive methods can be formulated as inclusion complexes, such as cyclodextrin inclusion complexes, or liposomes.

The pharmaceutically acceptable carriers described herein, for example, vehicles, adjuvants, excipients, and diluents, are well-known to those who are skilled in the art and are readily available to the public. It is preferred that the pharmaceutically acceptable carrier be one which is chemically inert to the active compound(s) and one which has no detrimental side effects or toxicity under the conditions of use.

The choice of excipient will be determined in part by the particular compound, as well as by the particular method used to administer the composition. Accordingly, there is a variety of suitable formulations of the pharmaceutical composition of the present invention. The following formulations for oral, aerosol, parenteral, subcutaneous, intravenous, intramuscular, interperitoneal, rectal, and vaginal administration are exemplary and are in no way limiting.

Injectable formulations are among those formulations that are preferred in accordance with the present inventive methods. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238–250 (1982), and *ASHP Handbook on Injectable Drugs*, Toissel, 4th ed., pages 622–630 (1986)). It is preferred that such injectable compositions be administered intravenously, intratumorally (within the tumor), or peritumorally (near the outside of the tumor). It will be appreciated by one of skill in the art that various of the described injectable compositions are suitable for intratumoral and peritumoral administration.

Topical formulations are well-known to those of skill in the art. Such formulations are particularly suitable in the context of the present invention for application to the skin.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The present inventive compound, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The present inventive compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral.

Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-b-aminopropionates, and 2-alkyl-imidazoline quaternary ammonium salts, and (e) mixtures thereof.

The parenteral formulations will typically contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the present inventive compounds, or compositions containing those compounds, can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

Method of Treating Cancer

The present inventive compound can be used for any suitable purpose. For example, the present inventive compound can be used for scientific and research purposes, such as in determining the types of cancer which can be treated and the onset of which can be delayed or the progress of which can be slowed by administration of the present inventive compound(s).

The present inventive compound has particular usefulness in applications in vivo. For example, the present inventive compound can be used in the prevention, delay of onset, slowing of progress, or treatment of cancer.

The present inventive method of treating cancer in a mammal, which is preferably a human, comprises administering to a mammal having cancer an effective amount, i.e., an anticancer effective amount, of a compound of the present invention. A preferred compound for use in the present inventive method of treating cancer is a compound comprising a protein or a polypeptide covalently bonded to 17-demethoxy-17-amino-geldanamycin or a derivative thereof, particularly wherein the derivative comprises a protein or polypeptide that binds to the surface of a cancer cell, or wherein the derivative is zwitterionic. Preferably, a protein or polypeptide bonded to 17-demethoxy-17-amino-geldanamycin or a derivative thereof, is bonded via a bifunctional linking molecule comprising a thio ether. Preferably, the protein or polypeptide binds to an antigen. Also, the compound is preferably internalized by the cell to which it is bound.

The method of treating cancer using the compound of the present invention can be made more effective by administering one or more other anticancer compounds along with one or more other compounds of the present invention. These other anticancer compounds include, but are not limited to, all of the known anticancer compounds approved for marketing in the United States and those that will become approved in the future. See, for example, Table 1 and Table 2 of Boyd, Current Therapy in Oncology, Section I. Introduction to Cancer Therapy (J. E. Niederhuber, ed.), Chapter 2, by B.C. Decker, Inc., Philadelphia, 1993, pp. 11–22. More particularly, these other anticancer compounds include doxorubicin, bleomycin, vincristine, vinblastine, VP-16, VW-26, cisplatin, carboplatin, procarbazine, and taxol for solid tumors in general; alkylating agents, such as BCNU, CCNU, methyl-CCNU and DTIC, for brain or kidney cancers; and antimetabolites such as 5-FU and methotrexate for colon cancer.

One skilled in the art will appreciate that suitable methods of administering compositions comprising the present inventive compound to an animal, such as a mammal, in particular a human, are available, and, although more than one route can be used to administer a particular compound, a particular route can provide a more immediate and more effective reaction than another route. Accordingly, the herein-described methods are exemplary and are in no way limiting.

The dose administered to an animal, such as a mammal, in particular a human, should be sufficient to prevent cancer, delay its onset, or slow (or stop) its progression. One skilled in the art will recognize that dosage will depend upon a variety of factors including the strength of the particular compound employed, as well as the age, species, condition, and body weight of the animal. The size of the dose will also be determined by the route, timing, and frequency of administration as well as the existence, nature, and extent of any adverse side-effects that might accompany the administration of a particular compound and the desired physiological effect.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. The present inventive method will typically involve the administration of about 0.1 to about 100 mg of one or more of the compounds described above per kg body weight.

Method of Producing a Water-Soluble Drug

The present inventive method of rendering soluble in water a water-insoluble drug comprises contacting a water-insoluble drug comprising a side-chain that can react with a bifunctional linking molecule, such as one that comprises a maleimido functional group, to obtain a first derivative of the water-insoluble drug comprising a reactive maleimido side chain. Then, by contacting the first derivative with a polar moiety comprising a thio moiety (X-SH), a water-soluble compound of the formula

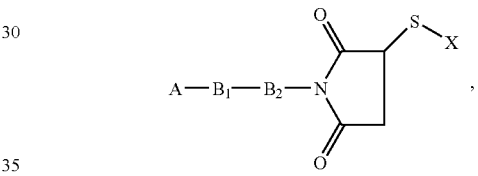

or a pharmaceutically acceptable salt thereof, is obtained, wherein A is the water-insoluble drug, $B_1$ and $B_2$ together are a spacer moiety, and X is a polar moiety. The water-insoluble drug, spacer moiety, and polar moiety are as previously described.

The water-insoluble drug optionally can be first reacted with a modifying agent to provide the aforementioned side-chain on the drug. The modifying agent can be any suitable agent that can produce a side-chain on the water-insoluble drug that can react with a bifunctional linking molecule. Preferably, the water-insoluble drug comprises a reactive methoxyaryl moiety, e.g., a methoxyquinone, that can react with a modifying agent comprising a primary amine. Reaction of the water-insoluble drug with the modifying agent then provides a demethoxy derivative of the water-insoluble drug in which the side-chain comprises a primary or secondary amine that can react with a bifunctional linking molecule. One preferred modifying agent is a diaminoalkyl, e.g., a $C_1$–$C_{20}$ alkyl comprising an amine on the first and an ultimate carbon, and is more preferably 1,3-diaminopropane or 1,4-diaminobutane While any one suitable bifunctional linking molecule can be used in conjunction with the present invention as described above, the linking molecule optionally can be selected from the group consisting of N-γ-maleimidobutyryloxy-succinimide ester (GMBS), sulfo-N-γ-maleimidobutyryloxysuccinimide ester (sulfo-GMBS), m-maleimidobenzoyl-N-hydroxysuccinimide ester (MBS), m-maleimidobenzoyl-N-hydroxysulfosuccinimide ester (sulfo-MBS), succinimidyl-4-[p-maleimidophenyl]butyrate (SMPB), sulfosuccinimidyl-4-[p-maleimidophenyl]butyrate (sulfo-SMPB), succinimidyl-4-[N-maleimidomethyl]cyclohexane-1-carboxylate (SMCC), sulfosuccinimidyl-4-[N-maleimidomethyl]cyclohexane-1-carboxylate (sulfo-SMCC), 4-[N-maleimidomethyl]-cyclohexane-1-carboxylhydrazide-HCl (M2C2H), and 4-[4-maleimidophenyl]-butyric acid hydrazide-HCl (MPBH). Most preferably, the bifunctional linking molecule is sulfo-N-γ-maleimidobutyryloxysuccinimide ester (sulfo-GMBS).

Method of Making a Water-Soluble Geldanamycin

Geldanamycin (1 of FIG. 1) comprises a 17-methoxy moiety that is reactive with a primary amine in an organic solvent. Accordingly, any 17-methoxy geldanamycin or its derivative can be reacted with a primary amine to give a geldanamycin analogue that is reactive with a polar moiety or a functional group of a mono- or bi-functional molecule or linking molecule. Example 2 depicts various reaction schemes that can be used by those skilled in the art to make the present inventive compounds. FIG. 1 illustrates a reaction of 3-amino-n-propylamine with geldanamycin. The 3-amino-N-propylamine can be replaced with 3-sulfhydryl-n-propylamine to create a geldanamycin that is reactive with succinimidyl functional groups, rather than the maleimidyl functional group illustrated in FIG. 1. Alternatively, lysine, or preferably α-amino blocked-lysine (which can optionally be de-blocked subsequently), can be directly reacted with geldanamycin to make a water-soluble derivative of geldanamycin, wherein the lysinyl residue is the polar moiety, and wherein the polar moiety is ionic or zwitterionic. Additionally, the solvent system used to contact the geldanamycin can be modified to facilitate the reaction. For example, when lysine is the primary amine and is contacted to geldanamycin, it is acceptable to use a 5:5:1 mixture of chloroform:methanol:water, and preferable to use a 1:1 mixture of chloroform:methanol. Of course, suitable substitutions for chloroform and methanol are within the spirit and scope of the present invention.

Various variations within the spirit and the scope of the present disclosure will be readily apparent to those of skill in the art. Moreover, any suitable, and preferably anticancer-effective, derivative of geldanamycin can be substituted for the geldanamycin. Such derivatives are well-known in the art. For example, U.S. Pat. No. 5,387,584 (to Schnur) and U.S. Pat. No. 4,261,989 (to Sasaki et al.) disclose geldanamycin derivatives and methods for making the same.

EXAMPLES

The following examples further illustrates the present invention but, of course, should not be construed as limiting the scope of the claimed invention in any way.

Example 1

This example illustrates the preparation of a water-soluble analogue of a water-insoluble drug in accordance with the present invention.

Geldanamycin 1 (see FIG. 1 for compounds referred to herein by number) was reacted with diaminopropane in chloroform to yield a mixture comprising 17-aminopropylaminogeldanamycin 2 by way of the following reaction. Geldanamycin (0.500 g, 0.0008918 mol) was dissolved in chloroform (200 ml). Diaminopropane (0.074 ml, 0.0008918 mol) was added dropwise to the reaction flask and stirred at room temperature. The reaction was monitored by thin layer chromatography (TLC) at regular intervals for the formation of the product.

Subsequent reaction of compound 2 with sulfo-N-g-maleimidobutyryloxysuccinimide ester (sulfo-GMBS) gave an intermediate 3 that could undergo Michael addition with compounds containing a thiol group. To accomplish this, a mixture of 17-aminopropylaminogeldanamycin 2 (0.1000 g, 0.000166 mol) and sulfo-GMBS (0.0951 g, 0.0002489 mol) were stirred in chloroform at room temperature. The reaction mixture was partitioned between chloroform (200 ml) and water (100 ml). The chloroform fraction was separated, dried with sodium sulfate, and concentrated to dryness to give 17-GMB-aminopropylaminogeldanamycin 3.

Compound 3 was reacted with L-cysteine to give the final product 17-cys-GMB-aminopropylaminogeldanamycin 4, which is water-soluble. To achieve the final product, a mixture of compound 3 (0.0500 g, 0.0000651 mol) and L-cysteine (0.0316 g, 0.00026 mol) was stirred in dimethylformamide (DMF) (4 ml) at room temperature overnight. The reaction was monitored on a silica TLC plate (10% MeOH/$CH_2Cl_2$) that showed the desired product to be a purple spot at the point of origin. The reaction mixture was concentrated by using ethanol to form an azeotrope with DMF to give the crude reaction mixture (0.1074 g).

The reaction mixture was purified on C18 solid-phase extraction (SPE) columns with water and methanol (MeOH). Twelve 6-ml C18 SPE columns were conditioned with MeOH (12 ml for each column) and water (12 ml for each column). Then the sample was dissolved in water (12 ml) and applied to the twelve SPE columns (1 ml solution for each column). Each of the columns was eluted with water (3 ml) and MeOH (6 ml). The combined MeOH fractions were concentrated to give the final product 4, which was found to be pure by NMR and FAB-MS analyses.

The analyses of compounds 2 through 4 were carried out by NMR and FAB-MS. Since there was a change of polarity from compound 3 to compound 4, it should be noted that compound 3 was analyzed in both $CD_2Cl_2$ and $d_4$-methanol for its comparison with compounds 2 and 4, respectively. Extensive 1D and 2D NMR analysis allowed the unequivocal assignment of most of the proton and carbon signals, except for carbons 29–32 in the five-membered ring. This was due to the fact that the thiol ether at carbon 30 was added from both sides of the plane of the ring, resulting in a diastereomeric pair. Therefore, carbons 24 through 34 showed two peaks and added further complexity in the spectrum. Taking the NMR and FAB-MS data as a complementary set, the structure for compound 4 was confirmed.

Additionally, the present example was repeated wherein diaminobutane was substituted for diaminopropane. This substitution facilitated reaction kinetics, and accordingly, is preferred for considerations pertaining to the efficiency of compound synthesis.

Thus, the present invention provides an exemplary reaction sequence that converts a water-insoluble compound (e.g., 1, geldanamycin) to a water-soluble compound e.g., 4, in four, or preferably three steps. The skilled artisan will appreciate that similar embodiments of the present invention can be readily discerned from the teachings of this example.

Example 2

This example illustrates nine reactions by which the chemical reactions set forth in Example 1 can be modified to arrive suitably at other compounds of the present invention. The general conditions of these reactions are known in the art and can be adapted to use in the context of the present invention without undue experimentation.

Part 1
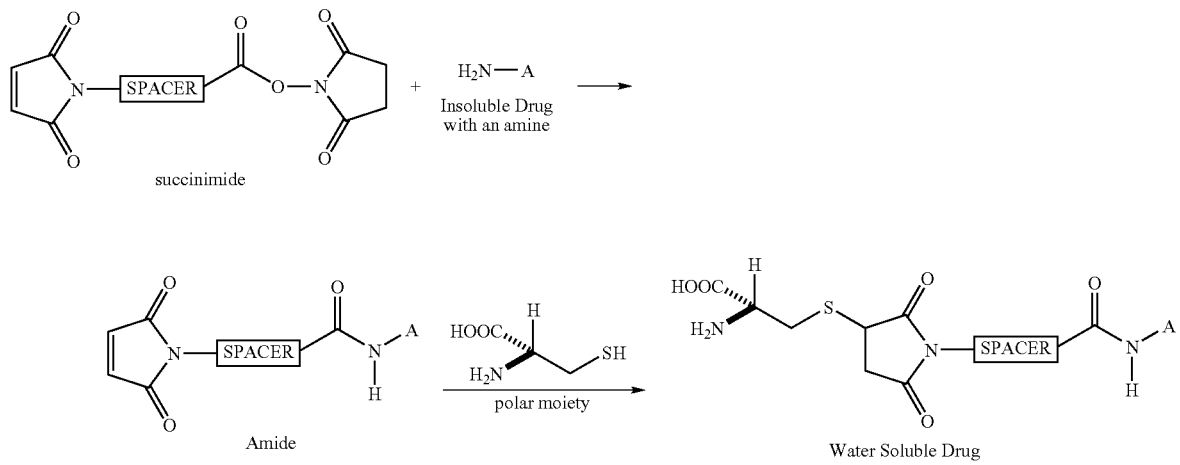
Part 2
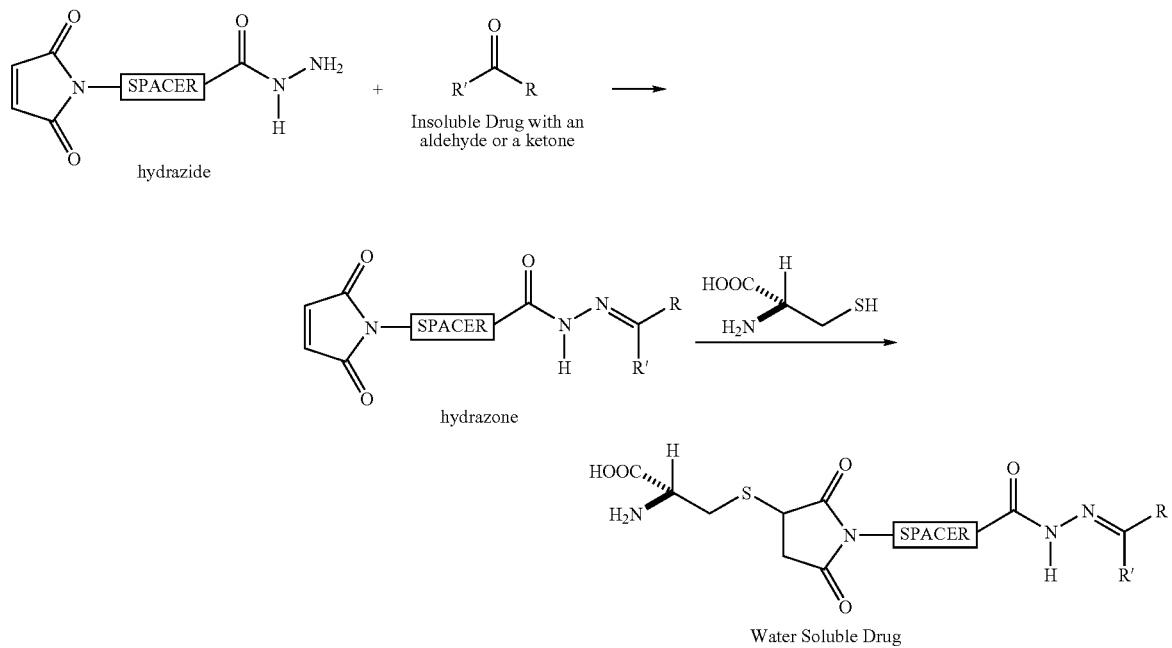
Part 3
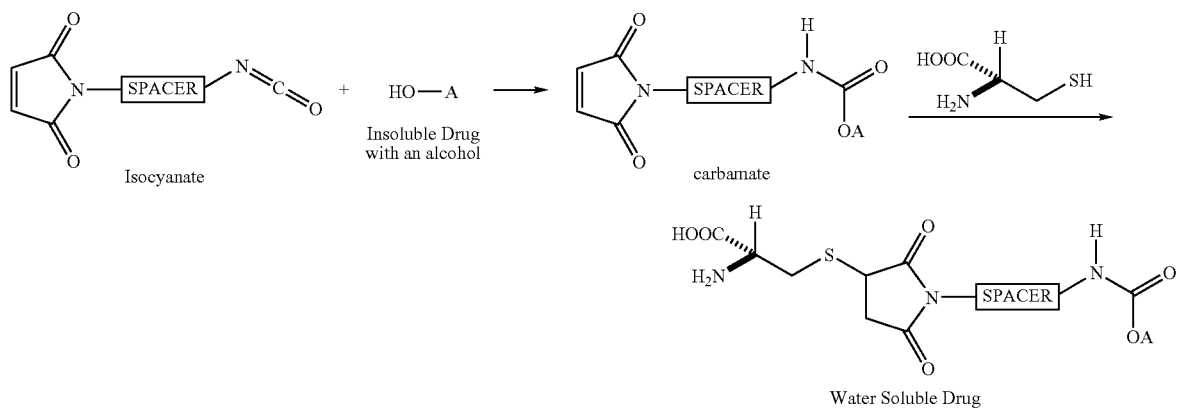

Part 4
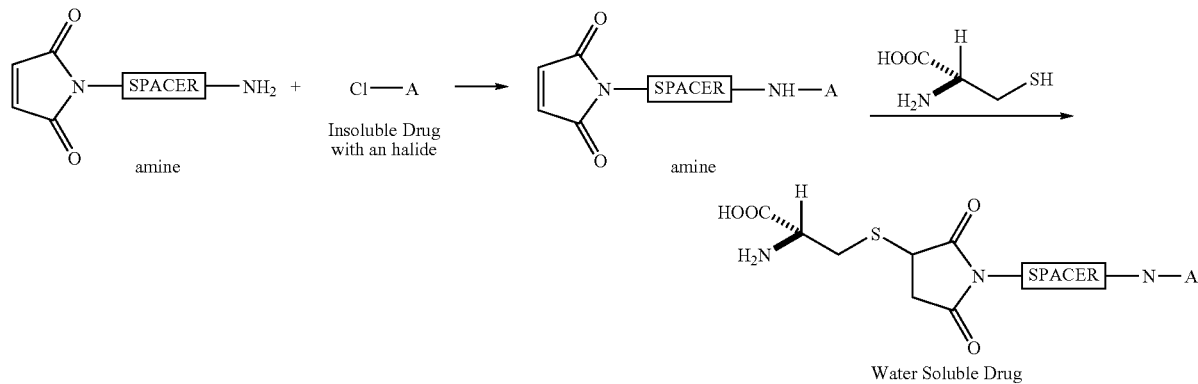
Part 5
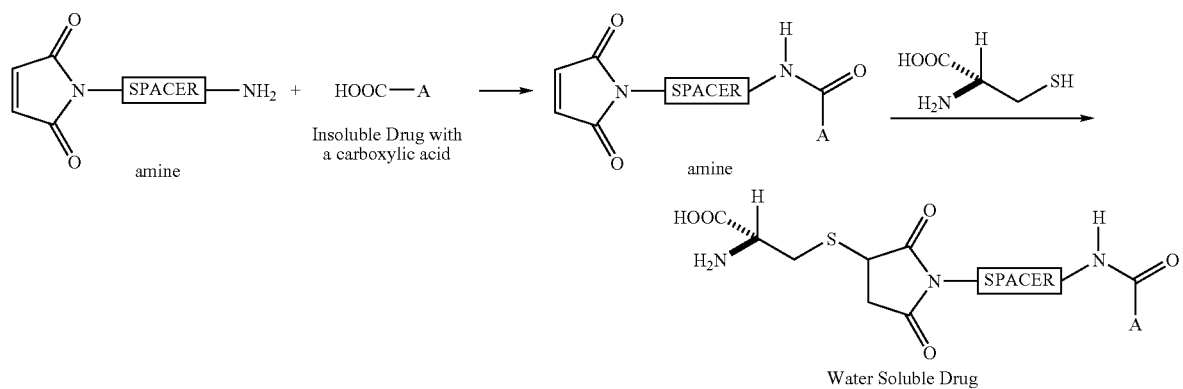
Part 6
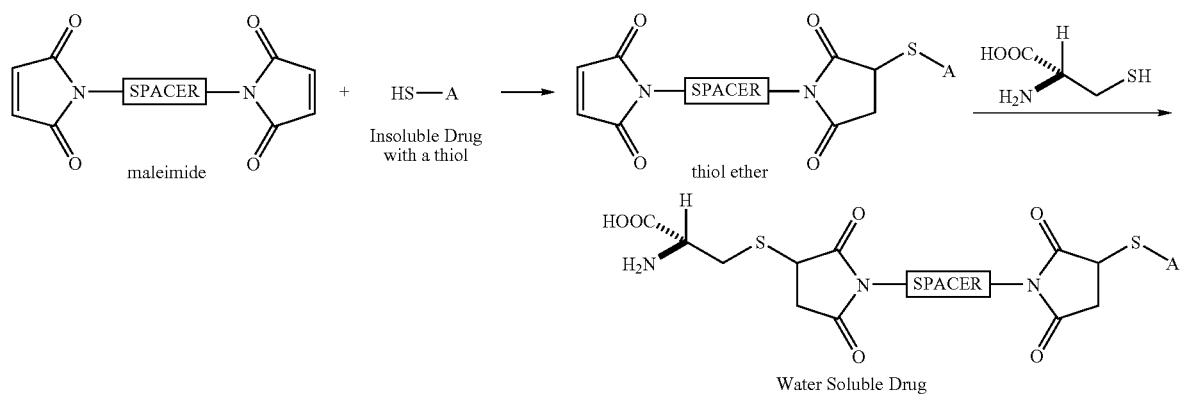
Part 7
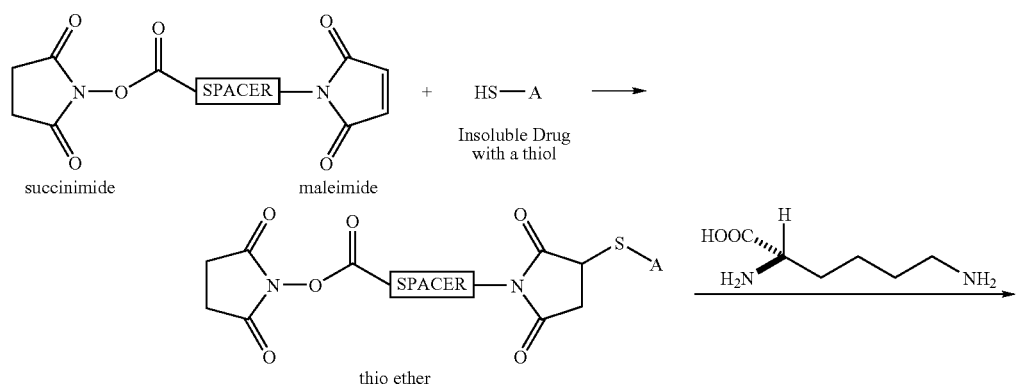

-continued

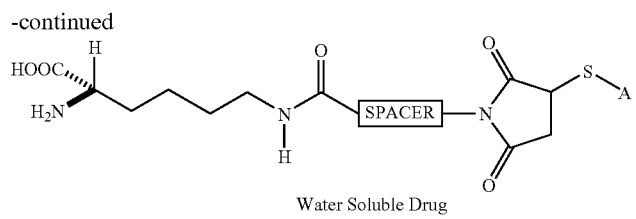

Water Soluble Drug

Part 8

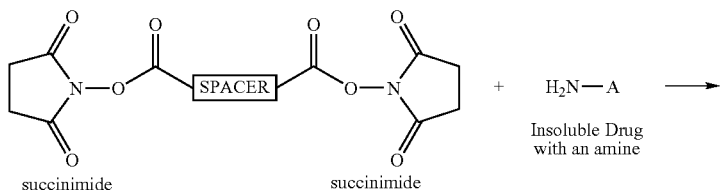

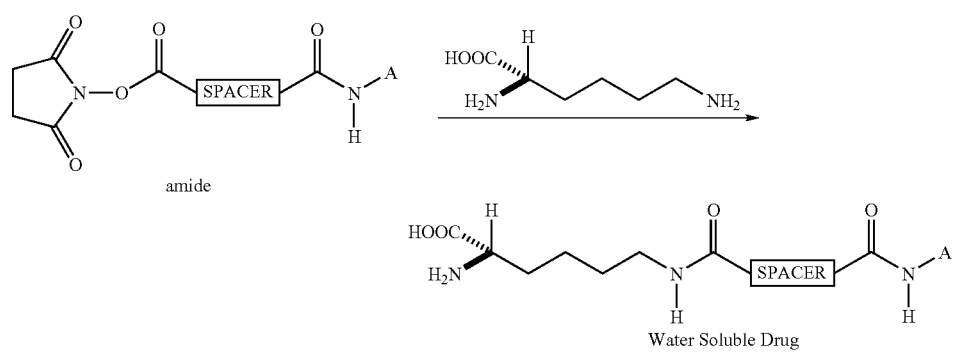

Part 9

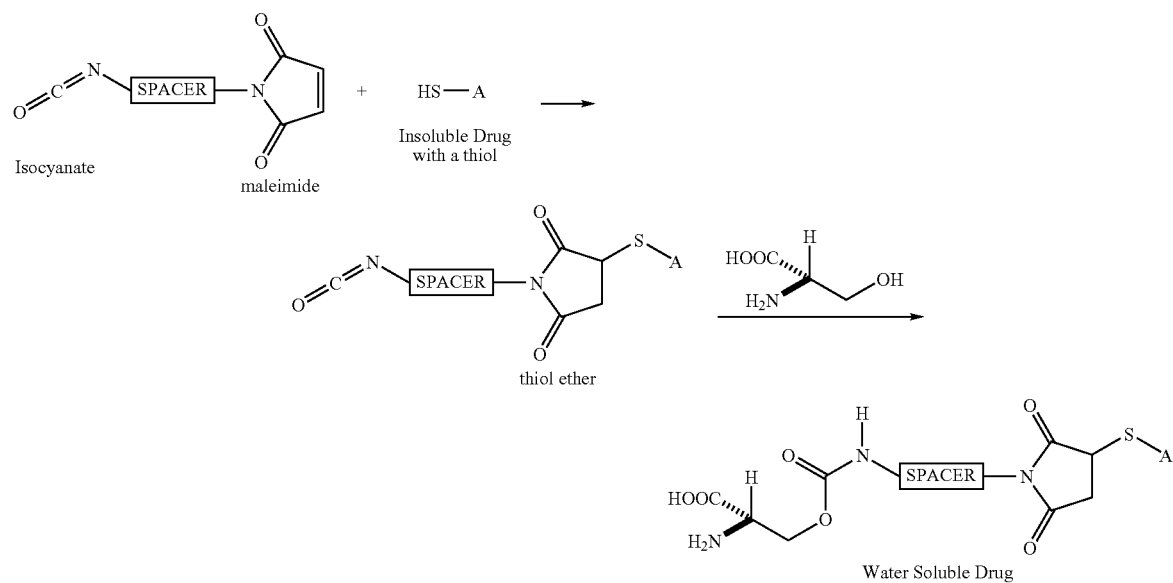

Example 3

This example demonstrates that suitable embodiments of the present inventive incorporating geldanamycin have a higher therapeutic index than insoluble geldanamycin, because of a higher solubility and a lower toxicity.

This example employs three antibodies, e21, AE1 (from Landolfi, Protein Design Labs, California), and anti-Tac (i.e., Zenapax from Hoffman-LaRoche, Inc., Nutley, N.J.). The antibodies e21 and AE1 bind Her2 with high affinity, and anti-Tac binds CD25 with high affinity. All three antibodies were radiolabeled and incubated with cells expressing the respective ligands on their cell surfaces (N87 cells for e21 and AE1 and HuT102 cells for anti-Tac). Both N87 cells and HuT102 cells are cancer cells that are known to be sensitive to the effects of geldanamycin. (HuT102 cells are cultured cells from an ATL patient available from the inventor's laboratories.) The cells were washed with dilute acid to remove unincorporated radiolabel, and the amount of radiolabel remaining in the cells was measured as an indication of the amount of antibody internalized.

For e21, 10% of the radiolabel was taken up by N87 cells, while for AE1 cells only 0% to 2% of radiolabel was taken up by N87 cells. For anti-Tac, no significant quantity of radiolabel was taken up by HuT102 cells. Accordingly, e21 is efficiently internalized by cells expressing Her2 on the cell surface, whereas AE1 and anti-Tac are not internalized in significant quantities.

N87 cells were separately treated with e21, geldanamycin, and a present inventive selectively targeted geldanamycin comprising e21 and geldanamycin ("e21:geldanamycin conjugate"; per the method depicted in FIG. 1, except that the e21 antibody was treated with Traut's reagent to generate free sulfhydryl groups). The e21 antibody alone did not have a substantial effect on the proliferation of N87 cells, which was measured by tritiated-thymidine incorporation (a standard method in the art). Geldanamycin inhibited 50% of the N87 proliferation at a concentration of 8 nanomolar; 17-aminopropylamino-geldanamycin at 180 nanomolar. In contrast, the e21:geldanamycin conjugate inhibited 50% of the N87 proliferation at a concentration of about 300 nanomolar. Thus, both geldanamycin and the e21:geldanamycin conjugate effectively inhibit the growth of N87 cells, which express a receptor (Her2) for e21. However, in a clinical setting, unconjugated geldanamycin is toxicity-limited, due to its tendency to precipitate in a mammal's blood and to cause anaphylaxis and other serious side effects. Accordingly, conjugated e21:geldanamycin can be administered at a much higher concentration, which will be seen to give rise to a higher therapeutic index relative to unconjugated geldanamycin.

In contrast, AE1 similarly conjugated to geldanamycin did not inhibit N87 proliferation by more than about 25%. Similarly, HuT102 cells, which are sensitive to the effects of geldanamycin, were not substantially inhibited by an anti-Her2:geldanamycin conjugate made in accordance with the method disclosed above. These data show that selectively targeted geldanamycin conjugates have a markedly reduced effect on cells that do not bind to the conjugate. Accordingly, the toxicity to non-targeted cells is substantially reduced. This, of course, allows the skilled clinician to administer more of the drug to a mammal in need thereof, and further increases the therapeutic index of the present inventive selectively targeted geldanamycin.

Example 4

This example demonstrates that 17-demethoxy-17-aminoderivatives of geldanamycin are effective inhibitors of cancer cell growth. N87 cells were exposed to the 17-demethoxy-17-aminoderivative of geldanamycin indicated in Table 1 below, and the concentration at which the proliferation of the N87 cells was inhibited by 50% was determined in nanomolar units.

TABLE 1

| 17-substituent | IC50 (nM) |
| --- | --- |
| $OCH_3$(geldanamycin) | 8.4 |
| $NH(CH_2)_3NH_2$ | 180 |
| $NH_2$ | 8.3 |
| $NHCH_2CH=CH_2$ | 5.7 |
| $NH(CH_2)_2Cl$ | 0.6 |
| $NH(CH_2)_2OH$ | 76 |
| $NH(CH_2)_2NH_2$ | Not effective |

All publications cited herein are hereby incorporated by reference to the same extent as if each publication was individually and specifically indicated to be incorporated by reference and was set forth in its entirety herein.

While the foregoing invention has been described in some detail for purposes of clarity and understanding, it will be appreciated by one skilled in the art from a reading of this disclosure that various changes in form and detail can be made without departing from the true spirit and scope of the invention as defined by the claims herein.

What is claimed is:

1. A water-soluble compound of the formula

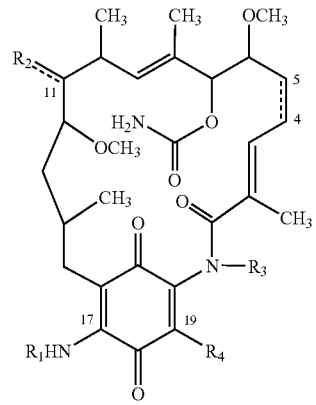

or a pharmaceutically acceptable salt thereof, wherein:

$R_1$ is a charged aliphatic moiety at neutral pH, which optionally is substituted by an aryl ring, wherein said aliphatic moiety is substituted by one or more charged moieties, which can be the same or different, selected from the group consisting of carbamate, carbonate, phosphamate, phosphate, phosphonate, pyrophosphate, triphosphate, sulfamate, sulfate, a $C_1$–$C_8$ monoalkylamine that is protonated at neutral pH, a $C_1$–$C_4$ dialkylamine that is protonated at neutral pH, and a $C_1$–$C_4$ trialkylammonium, $R_2$ is a halo or an —$OR_8$ when there is a single bond between $R_2$ and the carbon at position 11, wherein $R_8$ is selected from the group consisting of hydrogen, a $C_1$–$C_8$ alkylamido, a $C_1$–$C_8$ alkyl, a $C_2$–$C_8$ alkenyl, a $C_2$–$C_8$ alkynyl, a $C_1$–$C_8$ hydroxyalkyl, a $C_1$–$C_8$ alkyl carbamoyl, a $C_1$–$C_8$ alkylcarbonyl, and an aralkyl, any of which $R_8$ groups can be further substituted with one or more substituents, which can be the same or different, selected from the group consisting of nitro, halo, azido, hydroxy, amido and amino, or $R_2$ is oxo (=O) or oximino (=NOH) when there is a double bond between $R_2$ and the carbon at position 11, $R_3$ is selected from the group consisting of hydrogen and a group of the formula

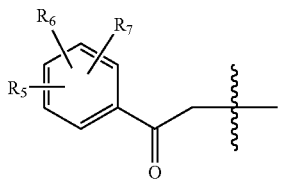

wherein $R_5$, $R_6$, and $R_7$ are each independently selected from the group consisting of hydrogen, a halo, an azido, a nitro, a $C_1$–$C_8$ alkyl, a $C_1$–$C_8$ alkoxy, an aryl, a cyano, and an $NR_{10}R_{11}R_{12}$, wherein $R_{10}$, $R_{11}$, and $R_{12}$ are each independently selected from the group consisting of hydrogen and a $C_1$–$C_3$ alkyl, $R_4$ is selected from the group consisting of hydrogen, a halo, a $C_1$–$C_8$ alkylamino, and a $C_1$–$C_8$ dialkylamino, and the bond between the carbons at positions 4 and 5 can be a single bond or a double bond.

2. The compound of claim 1, wherein $R_1$ is substituted by a member selected from the group consisting of a $C_1$–$C_{19}$ alkylamido, a $C_1$–$C_{19}$ alkyl, a $C_2$–$C_{19}$ alkenyl, a $C_2$–$C_{19}$ alkynyl, a $C_1$–$C_{19}$ hydroxyalkyl, a $C_1$–$C_{19}$ alkyl carbamoyl, a $C_1$–$C_{19}$ alkylcarbonyl, and an aralkyl, any of which can be further substituted with one or more substituents, which can be the same or different, selected from the group consisting of a nitro, a halo, an azido, a hydroxy, an amido, and an amino group.

3. The compound of claim 2, wherein $R_1$ is substituted by a member selected from the group consisting of a $C_1$–$C_7$ alkylamido, a $C_1$–$C_7$ alkyl, a $C_2$–$C_7$ alkenyl, a $C_2$–$C_7$ alkynyl, a $C_1$–$C_7$ hydroxyalkyl, a $C_1$–$C_7$ alkyl carbamoyl, a $C_1$–$C_7$ alkylcarbonyl, and a monocarbocyclic aralkyl any of which can be further substituted with one or more substituents, which can be the same or different, selected from the group consisting of a nitro, a halo, an azido, a hydroxy, an amido, and an amino group.

4. The compound of claim 2, wherein said aliphatic moiety comprises an amino acid.

5. The compound of claim 1, wherein $R_1$ is zwitterionic at neutral pH.

6. A pharmaceutical composition comprising a pharmaceutically acceptable carrier and a compound of claim 1.

7. A method of treating cancer in a mammal, wherein the cancer is selected from the group consisting of endometrial carcinoma, breast cancer, leukemia, gastrointestinal cancer, a central nervous system tumor and tongue carcinoma, wherein said method comprises administering to a mammal having said cancer an effective amount of a composition of claim 6.

8. A method of treating cancer in a mammal, wherein said method comprises administering to a mammal having cancer an anticancer effective amount of a composition of claim 6, whereupon the cancer in the mammal is treated, and wherein the cancer is gastric carcinoma or adult T-cell leukemia.

9. The method of claim 8, wherein the cancer is gastric carcinoma.

10. The method of claim 8, wherein the cancer is adult T-cell leukemia.

11. A water-soluble compound of the formula

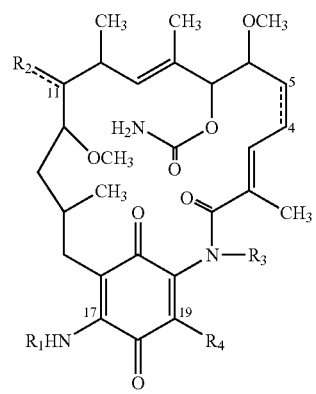

or a pharmaceutically acceptable salt thereof, wherein:

$R_1$ is a charged aliphatic moiety at neutral pH, which optionally is substituted by an aryl ring, wherein said aliphatic moiety is substituted by one or more charged moieties, which can be the same or different, selected from the group consisting of carbamate, carbonate, carboxylate, phosphamate, phosphate, phosphonate, pyrophosphate, triphosphate, sulfamate, sulfate, sulfonate, a $C_1$–$C_8$ monoalkylamine that is protonated at neutral pH, a $C_1$–$C_4$ dialkylamine that is protonated at neutral pH, and a $C_1$–$C_4$ trialkylanimonium, $R_2$ is a halo or an —$OR_8$ when there is a single bond between $R_2$ and the carbon at position 11, wherein $R_8$ is selected from the group consisting of a $C_1$–$C_8$ alkylamido, a $C_1$–$C_8$ alkyl, a $C_2$–$C_8$ alkenyl, a $C_2$–$C_8$ alkynyl, a $C_1$–$C_8$ hydroxyalkyl, a $C_{1-C8}$ alkyl carbamoyl, a $C_1$–$C_8$ alkylcarbonyl, and an aralkyl, any of which $R_8$ groups can be further substituted with one or more substituents, which can be the same or different, selected from the group consisting of nitro, halo, azido, hydroxy, amido and amino, or $R_2$ is oxo (=O) or oximino (=NOH) when there is a double bond between $R_2$ and the carbon at position 11, $R_3$ is selected from the group consisting of hydrogen and a group of the formula

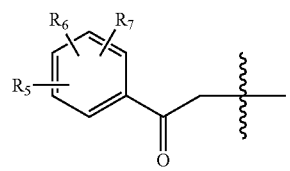

wherein $R_5$, $R_6$, and $R_7$ are each independently selected from the group consisting of hydrogen, a halo, an azido, a nitro, a $C_1$–$C_8$ alkyl, a $C_1$–$C_8$ alkoxy, an aryl, a cyano, and an $NR_{10}R_{11}R_{12}$, wherein $R_{10}$, $R_{11}$, and $R_{12}$ are each independently selected from the group consisting of hydrogen and a $C_1$–$C_3$ alkyl, $R_4$ is selected from the group consisting of hydrogen, a halo, a $C_1$–$C_8$ alkylamino, and a $C_1$–$C_8$ dialkylamino, and the bond between the carbons at positions 4 and 5 can be a single bond or a double bond.

12. A water-soluble compound of the formula

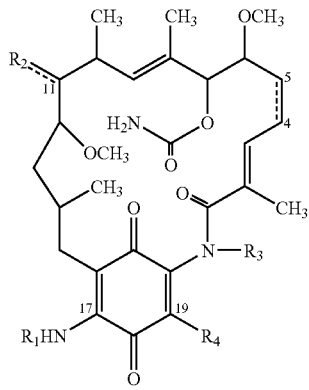

or a pharmaceutically acceptable salt thereof, wherein:
$R_1$ is a charged aliphatic moiety at neutral pH, which optionally is substituted by an aryl ring, wherein said aliphatic moiety is substituted by one or more charged moieties, which can be the same or different, selected from the group consisting of carbamate, carbonate, carboxylate, phosphamate, phosphate, phosphonate, pyrophosphate, triphosphate, sulfamate, sulfate, sulfonate, a $C_1$–$C_8$ monoalkylamine that is protonated at neutral pH, a $C_1$–$C_4$ dialkylamine that is protonated at neutral pH, and a $C_1$–$C_4$ trialkylanimonium, $R_2$ is a halo or an —$OR_8$ when there is a single bond between $R_2$ and the carbon at position 11, wherein $R_8$ is selected from the group consisting of hydrogen, a $C_1$–$C_8$ alkylamido, a $C_1$–$C_8$ alkyl, a $C_2$–$C_8$ alkenyl, a $C_2$–$C_8$ alkynyl, a $C_1$–$C_8$ hydroxyalkyl, a $C_1$–$C_8$ alkyl carbamoyl, a $C_1$–$C_8$ alkylcarbonyl, and an aralkyl, any of which $R_8$ groups can be further substituted with one or more substituents, which can be the same or different, selected from the group consisting of nitro, halo, azido, hydroxy, amido and amino, or $R_2$ is oxo (═O) or oximino (═NOH) when there is a double bond between $R_2$ and the carbon at position 11, $R_3$ is selected from the group consisting of a group of the formula

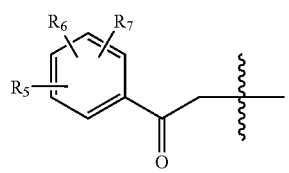

wherein $R_5$, $R_6$, and $R_7$ are each independently selected from the group consisting of hydrogen, a halo, an azido, a nitro, a $C_1$–$C_8$ alkyl, a $C_1$–$C_8$ alkoxy, an aryl, a cyano, and an $NR_{10}R_{11}R_{12}$, wherein $R_{10}$, $R_{11}$, and $R_{12}$ are each independently selected from the group consisting of hydrogen and a $C_1$–$C_3$ alkyl, $R_4$ is selected from the group consisting of hydrogen, a halo, a $C_1$–$C_8$ alkylamino, and a $C_1$–$C_8$ dialkylamino, and the bond between the carbons at positions 4 and 5 can be a single bond or a double bond.

13. A water-soluble compound of the formula

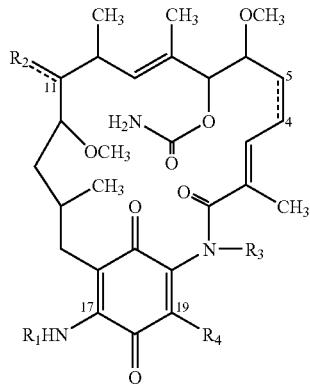

or a pharmaceutically acceptable salt thereof, wherein:
$R_1$ is a charged ahiphatic moiety at neutral pH, which optionally is substituted by an aryl ring, wherein said aliphatic moiety is substituted by one or more charged moieties, which can be the same or different, selected from the group consisting of carbamate, carbonate, carboxylate, phosphamate, phosphate, phosphonate, pyrophosphate, triphosphate, sulfamate, sulfate, sulfonate, a $C_1$–$C_8$ monoalkylamine that is protonated at neutral pH, a $C_1$–$C_4$ dialkylamine that is protonated at neutral pH, and a $C_1$–$C_4$ trialkylanimonium, $R_2$ is a halo or an —$OR_8$ when there is a single bond between $R_2$ and the carbon at position 11, wherein $R_8$ is selected from the group consisting of hydrogen, a $C_1$–$C_8$ alkylamido, a $C_1$–$C_8$ alkyl, a $C_2$–$C_8$ alkenyl, a $C_2$–$C_8$ alkynyl, a $C_1$–$C_8$ hydroxyalkyl, a $C_1$–$C_8$ alkyl carbamoyl, a $C_1$–$C_8$ alkylcarbonyl, and an aralkyl, any of which $R_8$ groups can be further substituted with one or more substituents, which can be the same or different, selected from the group consisting of nitro, halo, azido, hydroxy, amido and amino, or $R_2$ is oxo (═O) or oximino (═NOH) when there is a double bond between $R_2$ and the carbon at position 11, $R_3$ is selected from the group consisting of hydrogen and a group of the formula

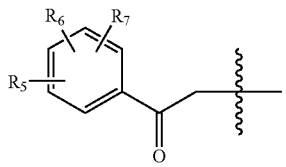

wherein $R_5$, $R_6$, and $R_7$ are each independently selected from the group consisting of hydrogen, a halo, an azido, a nitro, a $C_1$–$C_8$ alkyl, a $C_1$–$C_8$ alkoxy, an aryl, a cyano, and an $NR_{10}R_{11}R_{12}$, wherein $R_{10}$, $R_{11}$, and $R_{12}$ are each independently selected from the group consisting of hydrogen and a $C_1$–$C_3$ alkyl, $R_4$ is selected from the group consisting of a halo, a $C_1$–$C_8$ alkylamino, and a $C_1$–$C_8$ dialkylamino, and the bond between the carbons at positions 4 and 5 can be a single bond or a double bond.

14. The compound of claim 11, wherein $R_1$ is substituted by a member selected from the group consisting of a $C_1$–$C_{19}$ alkylamido, a $C_1$–$C_{19}$ alkyl, a $C_2$–$C_{19}$ alkenyl, a $C_2$–$C_{19}$ alkynyl, a $C_1$–$C_{19}$ hydroxyalkyl, a $C_1$–$C_{19}$ alkyl carbamoyl, a $C_1$–$C_{19}$ alkylcarbonyl, and an aralkyl, any of which can be further substituted with one or more substituents, which can be the same or different, selected from the group consisting of a nitro, a halo, an azido, a hydroxy, an amido, and an amino group.

15. The compound of claim 14, wherein $R_1$ is substituted by a member selected from the group consisting of a $C_1$–$C_7$ alkylamido, a $C_1$–$C_7$ alkyl, a $C_2$–$C_7$ alkenyl, a $C_2$–$C_7$ alkynyl, a $C_1$–$C_7$ hydroxyalkyl, a $C_1$–$C_7$ alkyl carbamoyl, a $C_1$–$C_7$ alkylcarbonyl, and a monocarbocyclic aralkyl any of which can be further substituted with one or more substituents, which can be the same or different, selected from the group consisting of a nitro, a halo, an azido, a hydroxy, an amido, and an amino group.

16. The compound of claim 14, wherein said aliphatic moiety comprises an amino acid.

17. The compound of claim 11, wherein $R_1$ is zwitterionic at neutral pH.

18. The compound of claim 12, wherein $R_1$ is substituted by a member selected from the group consisting of a $C_1$–$C_{19}$ alkylamido, a $C_1$–$C_{19}$ alkyl, a $C_2$–$C_{19}$ alkenyl, a $C_2$–$C_{19}$ alkynyl, a $C_1$–$C_{19}$ hydroxyalkyl, a $C_1$–$C_{19}$ alkyl carbamoyl, a $C_1$–$C_{19}$ alkylcarbonyl, and an aralkyl, any of which can be further substituted with one or more substituents, which can be the same or different, selected from the group consisting of a nitro, a halo, an azido, a hydroxy, an amido, and an amino group.

19. The compound of claim 18, wherein $R_1$ is substituted by a member selected from the group consisting of a $C_1$–$C_7$ alkylamido, a $C_1$–$C_7$ alkyl, a $C_2$–$C_7$ alkenyl, a $C_2$–$C_7$ alkynyl, a $C_1$–$C_7$ hydroxyalkyl, a $C_1$–$C_7$ alkyl carbamoyl, a $C_1$–$C_7$ alkylcarbonyl, and a monocarbocyclic aralkyl any of which can be further substituted with one or more substituents, which can be the same or different, selected from the group consisting of a nitro, a halo, an azido, a hydroxy, an amido, and an amino group.

20. The compound of claim 18, wherein said aliphatic moiety comprises an amino acid.

21. The compound of claim 12, wherein $R_1$ is zwitterionic at neutral pH.

22. The compound of claim 13, wherein $R_1$ is substituted by a member selected from the group consisting of a $C_1$–$C_{19}$ alkylamido, a $C_1$–$C_{19}$ alkyl, a $C_2$–$C_{19}$ alkenyl, a $C_2$–$C_{19}$ alkynyl, a $C_1$–$C_{19}$ hydroxyalkyl, a $C_1$–$C_{19}$ alkyl carbamoyl, a $C_1$–$C_{19}$ alkylcarbonyl, and an aralkyl, any of which can be further substituted with one or more substituents, which can be the same or different, selected from the group consisting of a nitro, a halo, an azido, a hydroxy, an amido, and an amino group.

23. The compound of claim 22, wherein $R_1$ is substituted by a member selected from the group consisting of a $C_1$–$C_7$ alkylamido, a $C_1$–$C_7$ alkyl, a $C_2$–$C_7$ alkenyl, a $C_2$–$C_7$ alkynyl, a $C_1$–$C_7$ hydroxyalkyl, a $C_1$–$C_7$ alkyl carbamoyl, a $C_1$–$C_7$ alkylcarbonyl, and a monocarbocyclic aralkyl any of which can be further substituted with one or more substituents, which can be the same or different, selected from the group consisting of a nitro, a halo, an azido, a hydroxy, an amido, and an amino group.

24. The compound of claim 22, wherein said aliphatic moiety comprises an amino acid.

25. The compound of claim 13, wherein $R_1$ is zwitterionic at neutral pH.

26. A pharmaceutical composition comprising a pharmaceutically acceptable carrier and a compound of claim 11.

27. A pharmaceutical composition comprising a pharmaceutically acceptable carrier and a compound of claim 12.

28. A pharmaceutical composition comprising a pharmaceutically acceptable carrier and a compound of claim 13.

29. A method of treating cancer in a mammal, wherein the cancer is selected from the group consisting of endometrial carcinoma, breast cancer, leukemia, gastrointestinal cancer, a central nervous system tumor and tongue carcinoma, wherein said method comprises administering to a mammal having said cancer an effective amount of a composition of claim 26.

30. A method of treating cancer in a mammal, wherein said method comprises administering to a mammal having cancer an anticancer effective amount of a composition of claim 26, whereupon the cancer in the mammal is treated, and wherein the cancer is gastric carcinoma or adult T-cell leukemia.

31. The method of claim 30, wherein the cancer is gastric carcinoma.

32. The method of claim 30, wherein the cancer is adult T-cell leukemia.

33. A method of treating cancer in a mammal, wherein the cancer is selected from the group consisting of endometrial carcinoma, breast cancer, leukemia, gastrointestinal cancer, a central nervous system tumor and tongue carcinoma, wherein said method comprises administering to a mammal having said cancer an effective amount of a composition of claim 27.

34. A method of treating cancer in a mammal, wherein said method comprises administering to a mammal having cancer an anticancer effective amount of a composition of claim 27, whereupon the cancer in the mammal is treated, and wherein the cancer is gastric carcinoma or adult T-cell leukemia.

35. The method of claim 34, wherein the cancer is gastric carcinoma.

36. The method of claim 34, wherein the cancer is adult T-cell leukemia.

37. A method of treating cancer in a mammal, wherein the cancer is selected from the group consisting of endometrial carcinoma, breast cancer, leukemia, gastrointestinal cancer, a central nervous system tumor and tongue carcinoma, wherein said method comprises administering to a mammal having said cancer an effective amount of a composition of claim 28.

38. A method of treating cancer in a mammal, wherein said method comprises administering to a mammal having cancer an anticancer effective amount of a composition of claim 28, whereupon the cancer in the mammal is treated, and wherein the cancer is gastric carcinoma or adult T-cell leukemia.

39. The method of claim 38, wherein the cancer is gastric carcinoma.

40. The method of claim 38, wherein the cancer is adult T-cell leukemia.

* * * * *

UNITED STATES PATENT AND TRADEMARK OFFICE
CERTIFICATE OF CORRECTION

| | |
|---|---|
| PATENT NO. | : 7,026,350 B2 |
| APPLICATION NO. | : 10/837785 |
| DATED | : April 11, 2006 |
| INVENTOR(S) | : Ho et al. |

It is certified that error appears in the above-identified patent and that said Letters Patent is hereby corrected as shown below:

ON THE TITLE PAGE:

Item (73) Assignee: "The United States of America as represented by the Department of Health and Human Services, Washington, DC (US)" should read --Government of the United States of America, represented by the Secretary, Department of Health and Human Services, Rockville, MD (US)--.

Signed and Sealed this

First Day of August, 2006

JON W. DUDAS
*Director of the United States Patent and Trademark Office*